United States Patent [19]
Ishida et al.

[11] Patent Number: 4,986,275
[45] Date of Patent: Jan. 22, 1991

[54] ULTRASONIC THERAPY APPARATUS

[75] Inventors: Akinori Ishida; Satoshi Aida, both of Kawasaki; Nobuyuki Iwama, Tokyo, all of Japan

[73] Assignee: Kabushiki Kaisha Toshiba, Kawasaki, Japan

[21] Appl. No.: 391,402

[22] Filed: Aug. 9, 1989

Related U.S. Application Data

[63] Continuation of Ser. No. 228,444, Aug. 5, 1988, abandoned.

[30] Foreign Application Priority Data

Aug. 5, 1987 [JP] Japan .............................. 62-194452
Sep. 30, 1987 [JP] Japan .............................. 62-249036

[51] Int. Cl.$^5$ ........................ A61B 8/14; A61B 17/22
[52] U.S. Cl. ................ 128/660.03; 128/24 A; 128/399
[58] Field of Search ..................... 128/24 A, 328, 399, 128/804, 660.03, 660.08, 660.09, 660.10; 606/662.03, 127, 128

[56] References Cited

U.S. PATENT DOCUMENTS

| | | | |
|---|---|---|---|
| 4,484,569 | 11/1984 | Driller et al. | 128/660.03 |
| 4,771,787 | 9/1988 | Wurster et al. | 128/660.03 |
| 4,787,394 | 11/1988 | Ogura | 128/660.03 |

FOREIGN PATENT DOCUMENTS

| | | | |
|---|---|---|---|
| 0111386 | 6/1984 | European Pat. Off. | 128/399 |
| 209966 | 5/1984 | Fed. Rep. of Germany | 128/662.03 |
| 3328068 | 2/1985 | Fed. Rep. of Germany | 128/328 |

OTHER PUBLICATIONS

Coleman et al., "Applications of Therapeutic Ultrasound . . . ", Progress in Medical Ultrasound, vol. 2, 1981, pp. 263–270.

*Primary Examiner*—Lee S. Cohen
*Attorney, Agent, or Firm*—Oblon, Spivak, McClelland, Maier & Neustadt

[57] ABSTRACT

An ultrasonic therapy apparatus includes a treating ultrasonic transducer, a driving section, an imaging ultrasonic transducer, a tomographic image forming section, and a position control section. The treating transducer is driven by the driving section, and generates a treating ultrasonic wave focused at a predetermined focal point in a body of an object to be examined. The imaging ultrasonic transducer is movably arranged, and transmits and receives an imaging ultrasonic wave for obtaining a tomographic image of the object to be examined. The tomographic image forming section drives the imaging transducer to transmit the imaging ultrasonic wave, and forms the tomographic image of the object to be examined based on an ultrasonic echo signal received by the imaging transducer. The position control section controls the position of the imaging ultrasonic transducer within a predetermined range along a line connecting a central point of the treating ultrasonic transducer and the focal point of the treating ultrasonic wave.

14 Claims, 6 Drawing Sheets

ULTRASONIC THERAPY APPARATUS

This application is a Continuation of application Ser. No. 07/228,444, filed on Aug. 5, 1988 now abandoned.

BACKGROUND OF THE INVENTION

1. Field of the Invention

The present invention relates to an ultrasonic therapy apparatus for treating a specific portion in a living body using ultrasonic energy.

2. Description of the Related Art

In recent years, an attempt has been made to treat an object to be examined as a living body, e.g., a patient using focused ultrasonic energy. Such a treatment includes lithotrity for breaking a calculus in a body and hyperthermia for heating and treating a cancer in a body.

A conventional ultrasonic therapy apparatus has an applicator comprising an ultrasonic transducer having a recessed surface, a treating transducer for forming an ultrasonic focal point at a geometrical central position of the recessed surface of the ultrasonic transducer, an ultrasonic transducer arranged to have a predetermined positional relationship with the treating transducer, and an imaging transducer for obtaining a tomographic image of an object to be examined (patient) using the ultrasonic transducer. In the ultrasonic therapy apparatus, a treatment target in a tomographic image is caused to coincide with the focal point of the treating transducer, and strong ultrasonic energy is radiated from the treating transducer to perform a treatment.

Ultrasonic energy is considerably attenuated in air and is not almost transmitted in air. In order to efficiently transmit the ultrasonic energy from the outside of a patient into a body, an ultrasonic medium liquid such as water having an appropriate acoustic impedance is interposed between the patient and the treating and imaging transducers.

Figure 1:
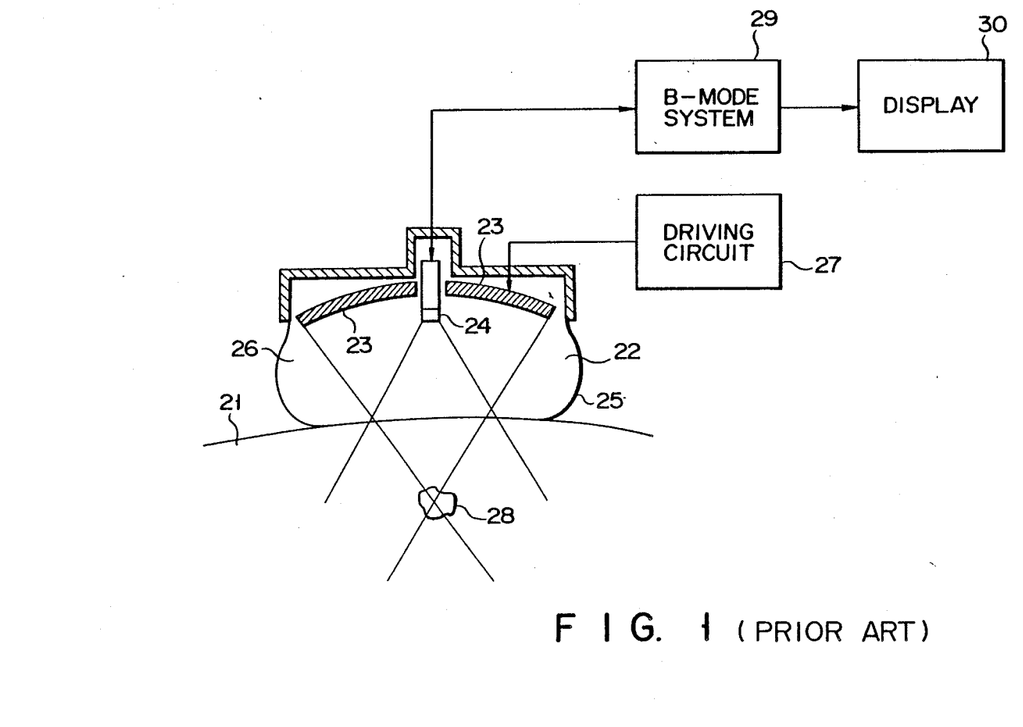
FIG. 1 is a diagram showing a schematic arrangement of a conventional ultrasonic therapy apparatus.

FIG. 1 shows a schematic arrangement of a conventional ultrasonic therapy apparatus. The ultrasonic therapy apparatus comprises water bag housing 22. In water bag housing 22, treating transducer 23 and imaging transducer 24 are arranged. Water bag housing 22 is sealed by membrane 25, and ultrasonic medium liquid (e.g., water) 26 having an appropriate acoustic impedance is filled in housing 22. Housing 22 is brought into tight contact with the body surface of patient 21, so that ultrasonic energy can be efficiently radiated into patient 21.

Treating transducer 23 is driven by driving circuit 27 connected thereto through a cable. When driving circuit 27 is started, transducer 23 produces a strong ultrasonic wave. The ultrasonic wave is focused at treatment target 28, and this portion is treated.

Imaging transducer 24 cooperates with B-mode control processing system 29 to perform sector electronic scanning, thereby obtaining a tomographic image in patient 21. Since imaging and treating transducers 24 and 23 are arranged to have a predetermined positional relationship, the focal point of treating transducer 23 permanently corresponds to an image position of the tomographic image obtained by imaging transducer 24, and is displayed as an appropriate mark, e.g., "x" on display 30 comprising a CRT display. The image of treatment target 28 is aligned with the position of the mark "x", and treating transducer 23 is driven, thus allowing a treatment of treatment target 28 using strong ultrasonic energy.

In the apparatus shown in FIG. 1, since imaging transducer 24 is arranged to be separated from the body surface of patient 21, treating energy is not disturbed during the treatment. However, a satisfactory result cannot be obtained when a treating state is to be observed. That is, an ultrasonic tomographic image obtained through imaging transducer 24 becomes unclear since an image is distorted due to multiplex reflection by membrane 25. For this reason, confirmation of the treating state or judgement of the treatment effect cannot often be satisfactorily made by using only the tomographic image obtained by the imaging transducer. In this apparatus, X-ray photography is performed after the treatment, and the treatment effect is judged using the X-ray photograph.

As described above, in the conventional ultrasonic therapy apparatus, although treating ultrasonic energy is not disturbed by the imaging transducer, a sufficiently clear tomographic image cannot be obtained by the imaging transducer. Therefore, this apparatus is unsatisfactory to allow confirmation of treating state during or after a treatment.

Summary of the Invention

It is an object of the present an ultrasonic therapy apparatus which can perform an efficient treatment without disturbing treating energy, can obtain a clear tomographic image, and can allow easy confirmation of a treatment effect and easy judgement of completion of a treatment.

In order to achieve the above object, an ultrasonic therapy apparatus according to the present invention comprises a treating ultrasonic transducer for generating a treating ultrasonic wave focused at a predetermined focal point in a body of an object to be examined, a driving section for driving the treating ultrasonic transducer, an imaging ultrasonic transducer, movably arranged, for transmitting and receiving an imaging ultrasonic wave so as to obtain a tomographic image of the object to be examined, a tomographic image forming section for driving the imaging ultrasonic transducer to transmit the imaging ultrasonic wave and forming a tomographic image of the object to be examined based on an ultrasonic echo signal received by the imaging ultrasonic transducer, and a position control section for controlling a position of the imaging ultrasonic transducer within a predetermined range along a line connecting a central point of the treating ultrasonic transducer and the focal point of the treating ultrasonic wave.

In the ultrasonic therapy apparatus of the present invention with the above-mentioned arrangement, in a treating operation mode, the imaging transducer is dodged from treating energy transmission path so as not to disturb a treating energy, thus allowing efficient radiation. In the ultrasonic therapy apparatus of the present invention, in a tomographic image forming mode, the imaging transducer is moved to a position adjacent to the body surface of the object to be examined so as to obtain a clear image free from distortion due to multiplex reflection or the like.

In the ultrasonic therapy apparatus of the present invention, since a marker indicating a focal point is also displayed on a tomographic image according to an operation of the position control section, the displayed marker is caused to coincide with a treatment target of the tomographic image, so that a proper treatment concentrated on a diseased portion can be performed.

According to the ultrasonic therapy apparatus of the present invention, an efficient treatment can be performed without disturbing treating energy, and a clear tomographic image can be obtained. In addition, confirmation of a treatment effect and judgement of completion of a treatment can be easily made.

Detailed Description of the Preferred Embodiment

An embodiment of the present invention will be described hereinafter with reference to the accompanying drawings.

Figure 2:
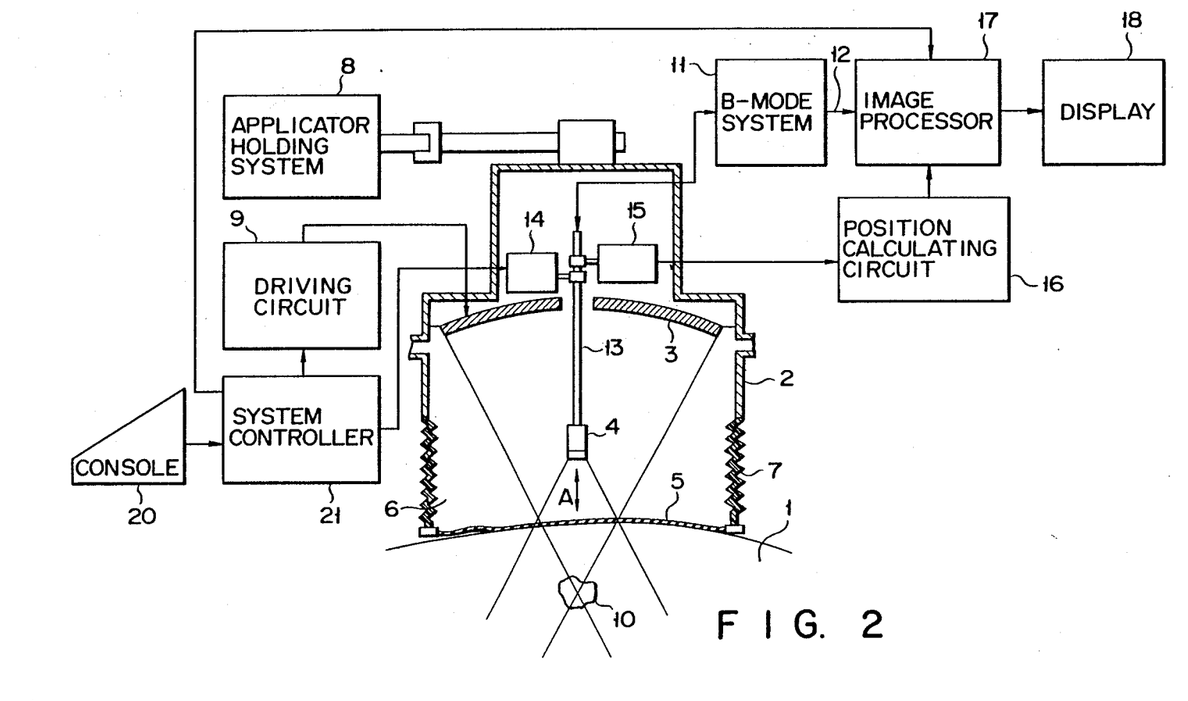
FIG. 2 is a diagram showing a schematic arrangement of an ultrasonic therapy apparatus according to an embodiment of the present invention.

FIG. 2 shows an arrangement of a lithotrite as an embodiment of an ultrasonic therapy apparatus according to the present invention.

The lithotrite comprises water bag housing 2, treating ultrasonic transducer 3, imaging ultrasonic transducer 4, membrane 5, ultrasonic medium liquid 6, bellows 7, applicator holding system 8, treating transducer driving circuit 9, B-mode control processing system 11, shaft 13, shaft driver 14, imaging transducer position detector 15, marker position calculating circuit 16, image processor 17, display 18, console 20, and system controller 21.

Figure 6:
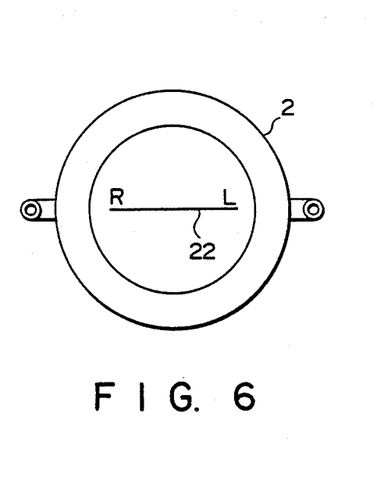
FIG. 6 is a view illustrating a scanning plane position mark attached to an applicator in the apparatus shown in FIG. 2.

Treating and imaging ultrasonic transducers 3 and 4 for lithotrity are disposed in water bag housing 2. The lower portion of housing 2 is a portion which is brought into contact with object to be examined (living body, e.g., patient) 1. Bellows 7 is formed on this portion, and an end face of this portion is sealed by membrane 5. Ultrasonic medium liquid (e.g., water) 6 having an appropriate acoustic impedance is filled in a sealed chamber formed by housing 2 having membrane 5 and bellows 7. Scanning surface mark 22 is attached to an upper outer surface of housing 2, as shown in FIG. 6. Scanning plane mark 22 consists of, e.g., a straight line indicating a position of a scanning plane of a tomographic image photographed by imaging transducer 4 and letters "L" and "R" indicating the left and right positions on a display screen. A portion including housing 2 and a portion including treating transducer 3, imaging transducer 4, medium liquid 6, shaft 13, shaft driver 14, and position detector 15 housed in housing 2 constitute an ultrasonic applicator. The applicator is held by applicator holding system 8. In use, the applicator is held such that the distal end of bellows 7 on the lower portion of housing 2, e.g., membrane 5 is brought into contact with the body surface of patient 1.

Treating transducer 3 is a lithotrity ultrasonic transducer comprising a transducer element which is formed into a recessed curved surface consisting of a semispherical surface having a diameter of 100 mm and a curvature of 160 mm. Treating transducer 3 is driven by treating transducer driving circuit 9, and produces ultrasonic wave pulses at a predetermined cycle and focuses strong ultrasonic energy at calculus 10 as a target to be broken located at the focal point.

Imaging transducer 4 cooperates with B-mode control processing system 11 to perform sector electronic scanning using an ultrasonic beam pulse, thereby obtaining tomographic image data in patient 1. For example, when imaging transducer 4 comprises an array transducer in which a plurality of transducer elements are arrayed, B-mode system 11 comprises a scanning circuit and a signal processor. The scanning circuit drives the transducer elements through corresponding delay circuits using a common pulse signal, thereby focusing and deflection-scanning an ultrasonic beam in accordance with delay times of the delay circuits. The signal processor fetches the signals from the transducer elements of imaging transducer 4 through the delay circuits, and performs processing including amplification and wave detection, thereby obtaining image signal 12 of a B-mode image.

Image signal 12 obtained through imaging transducer 4 becomes an optimal signal when imaging transducer 4 is brought into tight contact with the surface of patient 1 since no multiplex reflection occurs due to housing 2 and membrane 5. A distance (depth) of calculus 10 from the surface of patient 1 is not constant, and differs depending on a figure or physique of each patient 1 and on a portion where the calculus is present. However, the positional relationship between treating transducer 3 and the focal point of the treating ultrasonic wave is constant. In order to cause calculus 10 to coincide with the position of the focal point of treating transducer 3, the depth of housing 2 can be changed by expanding-/contracting bellows 7. Since an internal volume of housing 2 is also changed upon expansion/contraction of bellows 7, a liquid path and pump (neither are shown) coupled to housing 2 are provided, and the ultrasonic medium liquid inside housing 2 can be increased/decreased by the liquid path and the pump. Imaging transducer 4 must be moved to be brought into contact with the surface of patient 1 or to be dodged so as not to disturb breaking ultrasonic energy. For this purpose, imaging transducer 4 is coupled to shaft driver 14 comprising a stepping motor through shaft 13 to be movably held thereby. Shaft 13 is arranged along the central axis of treating transducer 3, and is reciprocated by shaft driver 14. Upon operation of shaft driver 14, treating transducer 3 is vertically moved within a predetermined range on a line connecting the central point of transducer 3 and the focal point thereof, as indicated by arrow A.

Position detector 15 employing a potentiometer is provided to shaft 13, and the moving distance of shaft 13, i.e., the moving distance of imaging transducer 4, is detected by position detector 15. The detection signal is input to marker position calculating circuit 16.

Marker position calculating circuit 16 calculates the position of the focal point of the ultrasonic wave from treating transducer 3 in an image of image signal 12 obtained by imaging transducer 4 based on the curvature of transducer 3 and the positional relationship between transducers 3 and 4. Transducers 3 and 4 are assembled to have a positional relationship determined by geometrical conditions in an initial state. A marker position signal for determining a marker position is set to be an initial value according to the predetermined positional relationship in the initial state. Thus, a moving distance detected by position detector 15, i.e., a moving distance by driver 14 can be added/subtracted to/from the initial value in the initial state, and a resultant value can be input to image processor 17. Marker position calculating circuit 16 outputs such a marker position signal. Image processor 17 has a digital scan converter, and converts and superimposes a marker signal for displaying a proper marker into a video signal in a television format based on B-mode image signal 12 and the marker position signal. Thereafter, processor 17 sends the obtained signal to display 18 having, e.g., a CRT display, thereby displaying a B-mode tomographic image of patient 1 and a focal point marker.

System controller 21 is operated in accordance with an operation of console 20 by an operator, and controls treating transducer driving circuit 9, shaft driver 14, and image processor 17.

A lithotrity operation in this apparatus will be described hereinafter.

Figure 3:
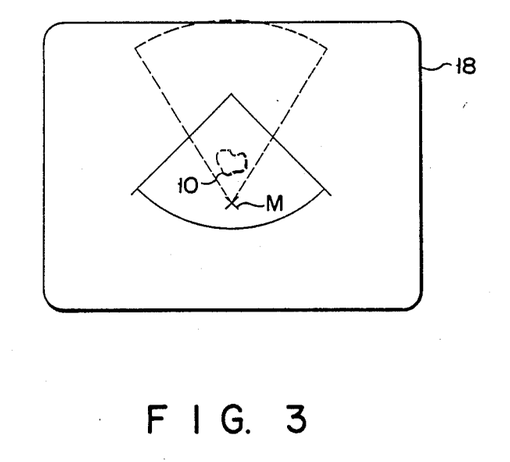
FIGS. 3 to 5 are views illustrating states of display screens for explaining an operation of the apparatus shown in FIG. 2.
Figure 4:
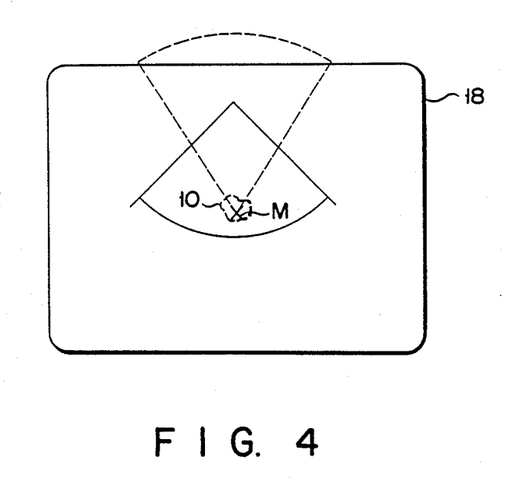
Figure 5:
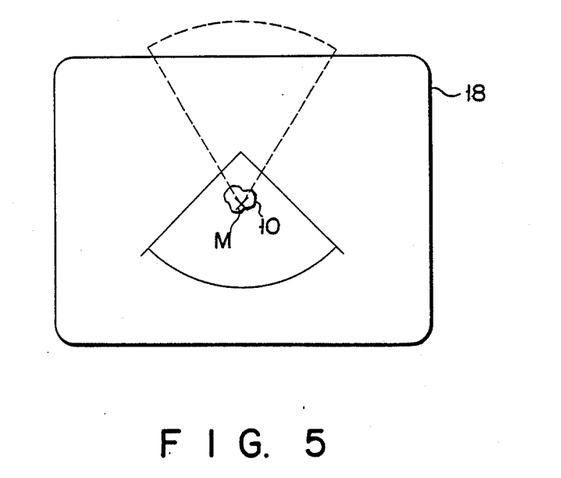

Although the position (depth) of calculus 10 differs depending on patient 1, as described above, imaging transducer 4 is set at an intermediate depth position in housing 2, and then, housing 2 is brought into contact with the body surface of patient 1. In this case, since the operator cannot observe the position and direction of the scanning plane where a tomographic image is photographed from outside housing 2, he sets housing 2 at an appropriate position of patient 1 with reference to scanning plane mark 22 displayed on housing 2. Then, display 18 is caused to display a tomographic image obtained by imaging transducer 4, as shown in FIG. 3, thereby displaying calculus 10. When no calculus 10 is displayed in the tomographic image, the positional relationship between housing 2 and patient 1 is adjusted with reference to scanning plane mark 22 while observing the displayed tomographic image. Then, housing 2 is moved by expanding/contracting bellows 7 so that focal point marker M on display 18 coincides with an image of calculus 10 (see FIG. 4). A tomographic image at this time is rather unclear due to multiplex reflection of water bag housing but positioning is made in this state. Imaging transducer 4 is moved downward in FIG. 2 to be set at contact position C at which transducer 4 is in contact with the body surface of patient 1 through only membrane 5. In this state, as shown in FIG. 5, a photographing region of a tomographic image is changed. However, since a clear tomographic image can be obtained, positioning between focal point marker M and an image of calculus 10 is accurately performed. Then, treating transducer driving circuit 9 is started.

Calculus 10 is broken while confirming a breaking state on display 18. When it is confirmed that breaking of calculus 10 is completed, a treatment is ended.

The lithotrity operation is performed such that breaking energy is radiated in response to an instruction operation of an operator, or breaking energy is continuously radiated at a predetermined frequency. While the breaking ultrasonic wave is generated, imaging transducer 4 is moved outside the breaking energy transmission path of treating transducer 3 in order to perform more effective lithotrity.

Figure 7:
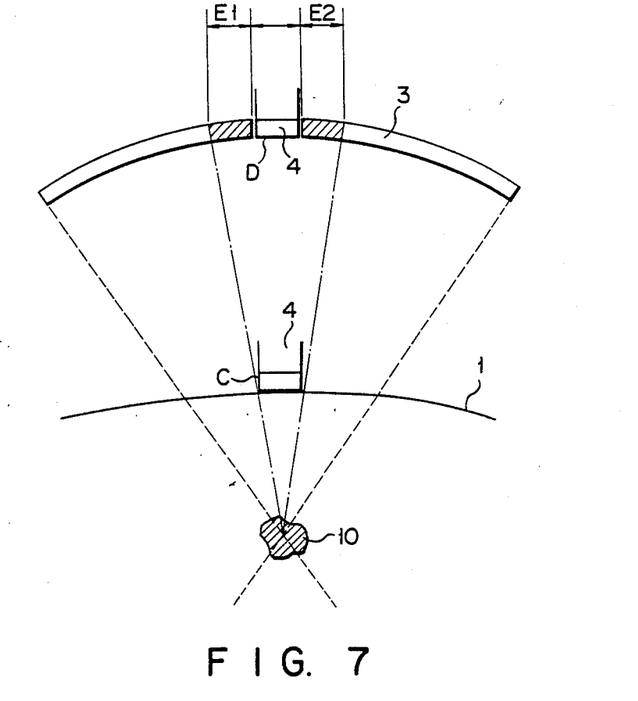
FIG. 7 is a view for explaining a function in the apparatus shown in FIG. 2.

More specifically, the operator operates console 20 to start the lithotrity operation. When the lithotrity operation is started, imaging transducer 4 is moved to dodge position D outside the breaking energy transmission path, e.g., a position coinciding with the surface of treating transducer 3, as shown in FIG. 7, and its moving distance is detected by position detector 15. In this case, the position of imaging transducer 4 before movement is stored in system controller 21. When write access to the digital scan converter of image processor 17 is stopped, a tomographic image displayed before movement is kept freeze-displayed on display 18.

After imaging transducer 4 is moved outside the breaking energy transmission path, treating transducer driving circuit 9 is driven, and a breaking energy pulse is radiated from transducer 3 to calculus 10. In this case, since imaging transducer 4 is located at dodge position D shown in FIG. 7, all the breaking energy from transducer 3 can be radiated onto patient 1. If transducer 4 is not moved and located at contact position C like in the conventional apparatus, the breaking energy beams from regions E1 and E2 of the central portion of transducer 3 are disturbed by imaging transducer 4 and are wasted.

In order to make up for the waste of breaking energy, it is necessary to use a larger treatment transducer, which inevitably results in an increase in the size of the applicator as a whole.

Further, imaging transducer 4 is located at contact portion C, the breaking energy may, in some cases, adversely influence an imaging operation of imaging transducer 4.

Then, imaging transducer 4 is returned to the position before movement, and a tomographic image is displayed in a real-time manner.

When radiation of breaking energy is instructed again, after imaging transducer 4 is dodged to a position outside the breaking energy transmission path, the breaking energy is radiated in the same manner as described above.

When continuous lithotrity is performed using continuous pulses, the operation can be performed as follows.

When a time required for moving imaging transducer 4 is shorter than a time interval of the continuous breaking pulses, i.e., transducer 4 can be moved within a pulse rest period, the above-mentioned operation can be performed synchronously with the continuous breaking pulses. More specifically, when approaching of transducer 4 to patient 1 and photographing display of an ultrasonic tomographic image, freezing of the ultrasonic tomographic image, and dodging of transducer 4 and radiation of breaking energy are alternately performed, a calculus can be effectively broken while observing a treatment state using a tomographic image of a diseased portion of patient 1 in a substantially real-time manner without disturbing breaking energy.

When a time required for moving transducer 4 is longer than a time interval of continuous breaking pulses, a rest period having an appropriate duration is formed for every several breaking pulses, and imaging transducer 4 is moved during this period to obtain a tomographic image. Thus, a lithotrity operation can be performed in a quasi-real-time manner.

When not lithotrity but a treatment by hyperthermia is performed, a continuous ultrasonic wave is often radiated instead of ultrasonic pulses. In this case, a rest period having an appropriate duration is formed for every predetermined period of time as in a case wherein a time required for moving transducer 4 is longer than a time interval of continuous breaking pulses in the above-mentioned lithotrity, and transducer 4 is moved during this interval to obtain a tomographic image. Thus, a hyperthermia operation can be performed in a quasi-real-time manner.

In the above description, imaging transducer 4 is moved between a position at which transducer 4 is brought into contact with patient 1 through membrane 5 and a position at which transducer 4 substantially coincides with the surface of treating transducer 3. However, the moving range of imaging transducer 4 is not particularly limited. Transducer 4 need only approach patient 1 when a tomographic image is photographed, and need only be dodged to a position so as not to disturb treating energy when a treating ultrasonic wave is produced.

The present invention is not limited to the abovementioned embodiment, and various changes and modifications may be made within the spirit and scope of the invention.

In the above embodiment, a transducer which is constituted by a single transducer element to obtain a predetermined curvature is used as the treating ultrasonic transducer. However, the treating ultrasonic transducer may employ a transducer in which a plurality of planer transducer elements are combined to form a recessed surface having a predetermined curvature (e.g., a plurality of transducer elements are bonded on a recessed surface having a predetermined curvature of a substrate), an annular array transducer constituted by a plurality of concentrical transducer elements, or a two-dimensional array transducer in which transducer elements are arranged in a matrix on a two-dimensional plane. The imaging ultrasonic transducer is not limited to a (linear) array transducer, but may be a mechanical transducer for mechanically scanning a single transducer element, an annular array mechanical scan transducer for mechanically scanning an annular array transducer, or a two-dimensional array transducer.

The case has been described wherein the imaging transducer position detector and the shaft driver are separately arranged. However, the number of pulses of a pulse motor for driving the shaft may be counted to detect a moving amount.

In the above embodiment, the bellows are used to position a calculus and the ultrasonic focal point. Instead, the treating and imaging ultrasonic transducers may be movably arranged in the water bag housing.

Figure 8:
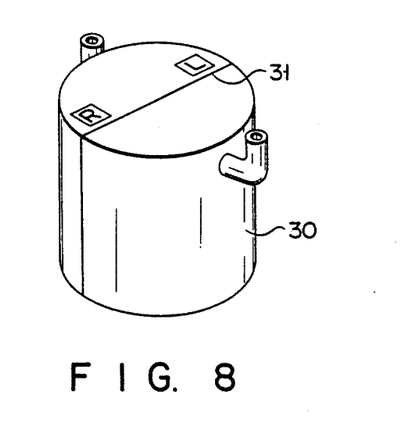
FIGS. 8 to 10 are views illustrating other embodiments of a mark attached to the applicator in the ultrasonic therapy apparatus according to the present invention.
Figure 9:
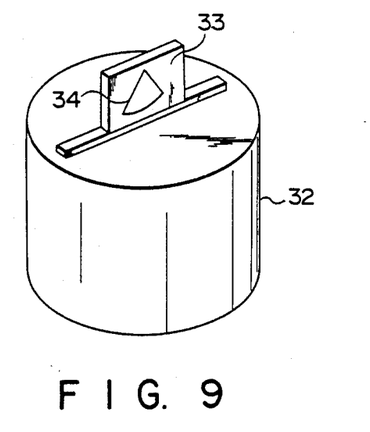

As a scanning plane mark indicating the position of a scanning plane by the imaging transducer, scanning plane mark 31 may be attached to extend from the upper surface to the outer peripheral surface of housing 30, as shown in FIG. 8 in place of scanning plane mark 22 attached to the upper surface of housing 2 of the applicator, as shown in FIG. 6. Alternatively, scanning plane mark portion 33 projecting from the upper surface of housing 32 as shown in FIG. 9 may be formed (in this case, although letters "L" and "R" indicating the left and right positions of the tomographic image on the display screen are preferably attached, if scanning plane mark 34 as shown in FIG. 9 is attached to only one side surface of the projection, the left and right positions on the display screen can be determined without providing letters "L" and "R").

Figure 10:
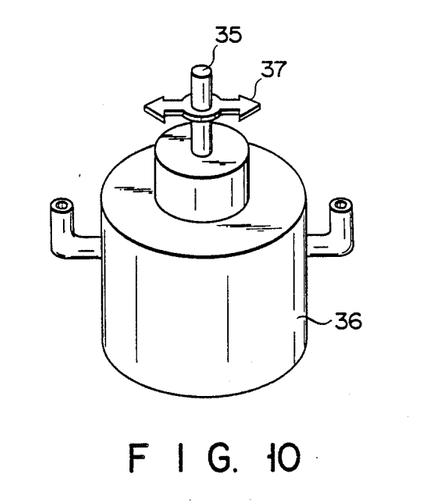

The imaging transducer is often pivotally arranged on the housing. In this case, as shown in FIG. 10, shaft 35 for holding the imaging transducer projects outward from the upper surface of housing 36 (while maintaining a sealed state inside housing 36, of course), and scanning plane mark 37 pivoting together with shaft 35 is provided to this portion.

Figure 11:
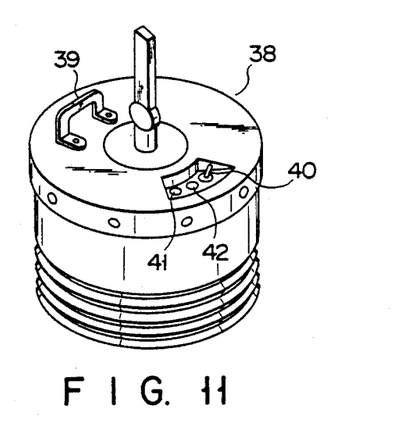
FIG. 11 is a view illustrating an arrangement of another embodiment of an applicator in the ultrasonic therapy apparatus according to the present invention.

As shown in FIG. 11, handle 39 for moving the applicator may be mounted on the outer surface of housing 38 where it is easy to access. Some of switches provided to console 20, e.g., holding switch 40 for holding the position of the applicator, treatment start switch 41 for instructing start of a treatment upon radiation of an ultrasonic energy, and treatment end switch 42 for instructing end of a treatment can be provided to the outer surface of housing 38 where easy operation is allowed. A switch for controlling an amount of an ultrasonic medium liquid inside the housing may be provided to the outer surface of the housing where easy operation is allowed. Of course, some of the handle and switches may be selectively arranged.

In the above embodiment, an ultrasonic lithotrite or an ultrasonic hyperthermia apparatus has been described. The present invention can be applied to other therapy apparatuses by radiation of an ultrasonic energy.

What is claimed is:

1. An ultrasonic therapy apparatus comprising:
a treating ultrasonic transducer for generating a treating ultrasonic wave focused at a predetermined focal point in a body of an object to be examined;
driving means for intermittently driving said treating ultrasonic transducer to generate the treating ultrasonic wave;
an imaging ultrasonic transducer, movably arranged, for transmitting and receiving an imaging ultrasonic wave so as to obtain a tomographic image of the object to be examined;
tomographic image forming means for driving said imaging ultrasonic transducer to transmit the imaging ultrasonic wave and forming a tomographic image of the object to be examined based on an ultrasonic echo signal received by said imaging ultrasonic transducer; and
position control means for cyclically moving said imaging ultrasonic transducer in association with said driving means between a first position near the body and a second position apart from the body along a line connecting a central point of said treating transducer and the focal point of the treating ultrasonic wave, the treating ultrasonic wave being generated when the image ultrasonic transducer is in the second position.

2. An apparatus according to claim 1, further comprising display means for displaying the tomographic image obtained by said tomographic image forming means, moving amount detecting means for detecting a moving amount of said imaging ultrasonic transducer moved by said position control means, and marker display means for causing said display means to superimpose and display a marker indicating the focal point on the tomographic image in accordance with the moving amount obtained by said moving amount detecting means.

3. An apparatus according to claim 1, wherein said second position is set so as not to disturb treating energy in a treatment operation by said treating ultrasonic transducer.

4. An apparatus according to claim 3, wherein said first position is a position at which said imaging ultrasonic transducer is brought into substantially tight contact with the object to be examined.

5. An apparatus according to claim 3, wherein said second position is a position at which the surface of said imaging ultrasonic transducer substantially is flush with the surface of said treating ultrasonic transducer.

6. An apparatus according to claim 1, wherein said driving means includes means for driving said treating ultrasonic transducer so that said treating ultrasonic transducer generates lithotrity ultrasonic energy.

7. An apparatus according to claim 1, wherein said driving means includes means for driving said treating ultrasonic transducer so that said treating ultrasonic transducer generates hyperthermia ultrasonic energy.

8. An apparatus according to claim 1, wherein said position control means includes means for removing said imaging ultrasonic transducer for each lithotrity operation.

9. An apparatus according to claim 1, wherein said position control means includes means for removing said imaging ultrasonic transducer for every predetermined number of lithotrity operations.

10. An apparatus according to claim 1, wherein said treating ultrasonic transducer and said imaging ultrasonic transducer are housed in a housing filled with an ultrasonic medium.

11. An ultrasonic therapy apparatus comprising:
a treating ultrasonic transducer for generating a treating ultrasonic wave focused at a predetermined focal point in a body of an object to be examined;
driving means for driving said treating ultrasonic transducer, said driving means including means for providing a predetermined rest period for every predetermined number of lithotrity operations;
an imaging ultrasonic transducer, movably arranged, for transmitting and receiving an imaging ultrasonic wave so as to obtain a tomographic image of the object to be examined;
tomographic image forming means for driving said imaging ultrasonic transducer to transmit the imaging ultrasonic wave and forming a tomographic image of the object to be examined based on an ultrasonic echo signal received by said imaging ultrasonic transducer; and
position control means for controlling a position of said imaging ultrasonic transducer within a predetermined range along a line connecting a central point of said treating transducer and the focal point of the treating ultrasonic wave, said position control means including means for moving said imaging ultrasonic transducer for each rest period and for removing said imaging ultrasonic transducer for every predetermined number of lithotrity operations.

12. An ultrasonic therapy apparatus comprising:
an applicator housing a treating ultrasonic transducer for generating a treating ultrasonic wave focused at a predetermined focal point in a body of an object to be examined, and an imaging ultrasonic transducer for transmitting and receiving an imaging ultrasonic wave for obtaining a B-mode tomographic image of the object to be examined;
driving means for driving said treating ultrasonic transducer;
tomographic image forming means for driving said imaging ultrasonic transducer to transmit the imaging ultrasonic wave and forming the B-mode tomographic image of the object to be examined based on an ultrasonic echo signal received by said imaging ultrasonic transducer; and
scanning plane indication means, arranged on the outside of said applicator for indicating a rotational position of a scanning plane of the B-mode tomographic image by said imaging ultrasonic transducer.

13. An apparatus according to claim 12, wherein said imaging ultrasonic transducer is movably arranged along a line connecting a central point of said treating ultrasonic transducer and the focal point of the ultrasonic wave, and said apparatus further comprises position control means for controlling a position of said imaging ultrasonic transducer within a predetermined range.

14. An ultrasonic therapy apparatus comprising:
a treating ultrasonic transducer for generating a treating ultrasonic wave focused at a predetermined focal point in a body of an object to be examined;
driving means for driving said treating ultrasonic transducer;
an imaging ultrasonic transducer, movably arranged, for transmitting and receiving an imaging ultrasonic wave so as to obtain a tomographic image of the object to be examined;
tomographic image forming means for driving said imaging ultrasonic transducer to transmit the imaging ultrasonic wave and forming a tomographic image of the object to be examined based on an ultrasonic echo signal received by said imaging ultrasonic transducer; and
position control means for controlling a position of said imaging ultrasonic transducer within a predetermined range along a line connecting a central point of said treating transducer and the focal point of the treating ultrasonic wave, said position control means including means for moving said imaging ultrasonic transducer for each lithotrity operation for a predetermined period of time;
wherein said driving means includes means for providing a predetermined rest period for each lithotrity operation for the predetermined period of time, and said position control means includes means for moving said imaging ultrasonic transducer for each rest period.

* * * * *